United States Patent [19]

Matson

[11] Patent Number: 4,904,804

[45] Date of Patent: Feb. 27, 1990

[54] PREPARATION OF 2-PYRROLIDONE

[75] Inventor: Michael S. Matson, Bartlesville, Okla.

[73] Assignee: Phillips Petroleum Company, Bartlesville, Okla.

[21] Appl. No.: 185,197

[22] Filed: Apr. 22, 1988

Related U.S. Application Data

[63] Continuation of Ser. No. 631,411, Jul. 16, 1984, abandoned.

[51] Int. Cl.$^4$ ............................................. C07D 201/08
[52] U.S. Cl. ..................................... 548/554; 548/543
[58] Field of Search ................................ 548/543, 554

[56] References Cited

U.S. PATENT DOCUMENTS

| | | | |
|---|---|---|---|
| 3,080,377 | 3/1963 | Lizo | 548/554 |
| 3,095,423 | 6/1963 | Copenhaver et al. | 548/554 |
| 3,781,298 | 12/1973 | Davis | 548/554 |
| 3,812,148 | 5/1974 | Hollstein et al. | 548/554 |

*Primary Examiner*—David B. Springer
*Attorney, Agent, or Firm*—Beverly M. Dollar

[57] ABSTRACT

Process is disclosed for the one reaction step preparation of 2-pyrrolidone by contacting with hydrogen, ammonia, at least one diluent and a catalyst consisting essentially of palladium on alumina; wherein the molar ratio of ammonia to succinic acid on succinic anhydride is about 1:1 to about 10:1.

9 Claims, No Drawings

PREPARATION OF 2-PYRROLIDONE

This application is a continuation of application Serial No. 631,411, filed July 16, 1984, abandoned.

BACKGROUND

This invention relates to the preparation of 2-pyrrolidone.

The conversion of anhydrides such as maleic anhydride and succinic anhydride to 2-pyrrolidone is known in the art. Various catalysts such as for example cobalt, nickel, ruthenium and palladium have been employed for this purpose. It has, however, generally been found that yields of less than about 60% of theory are obtained. In addition, although many catalysts and catalyst supports have been suggested for the process, the reaction has been demonstrated to be highly sensitive to both catalyst metal and support, as well as the ratios of the various reactants employed.

OBJECTS OF THE INVENTION

An object of the invention, therefore, is a process for the one-step conversion of succinic acid or succinic anhydide to 2-pyrrolidone in high yield.

This and other objects will become apparent from further study of the disclosure and claims herein provided.

STATEMENT OF THE INVENTION

In accordance with the invention, I have discovered that the yield of 2-pyrrolidone obtained by the reductive amination of succinic acid or succinic anhydride is surprisingly improved by employing a catalyst consisting essentially of palladium on alumina and a molar ratio of ammonia/succinic moiety of at least 1:1 up to 10:1 for the reductive amination reaction.

Thus, in accordance with the present invention, succinic acid or succinic anhydride is contacted with hydrogen and ammonia in the presence of at least one diluent and a catalyst consisting essentially of elemental palladium on alumina support under reaction conditions suitable for the production of 2-pyrrolidone. By the practice of the present invention, the conversion of succinic acid or succinic anhydride to 2-pyrrolidone, which requires several chemical conversion steps, can be carried out in one high-yield reaction step.

REACTANTS

One of the reaction components is ammonia, $NH_3$. The molar ratio of ammonia to succinic acid or succinic anhydride employed is an important variable in determining the yield of 2-pyrrolidone achieved in the practice of the invention. Thus, a molar ratio of at least 1:1 ($NH_3$ to succinic moiety) is generally employed. Molar ratios of up to about 10:1 are suitable. Preferably, molar ratios between about 1.5:1 and about 5:1 are employed, with molar ratios ranging from about 2.5:1 up to about 3.5:1 most preferred because best yields are obtained at such ratios.

Another required reaction component is hydrogen. The amount of hydrogen employed is not believed to be critical, and consequently can be employed in any suitable amount as readily determined by those of skill in the art. It is convenient to control the overall reaction pressure by controlling the amount of hydrogen charged. For purposes of guidance, it is suggested that a minimum reaction pressure be about 1000 psig with an upper limit defined only by practical considerations such as for example, equipment and operating costs. Preferably, reaction pressures of about 1000 up to about 5000 psig will be employed, with pressures ranging from about 1500 up to about 3000 psig most preferred. The most preferred range defines that pressure wherein efficient utilization of equipment and feed materials are coupled with high product yield.

DILUENT

The inventive one-step reductive amination of succinic acid or succinic anhydride is carried out in the presence of at least one diluent selected from the group consisting of:
water,
ethers having the formulae:

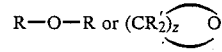

wherein each R is independently selected from $C_1$ up to about $C_{10}$ alkyl, cycloalkyl, aryl, aralkyl and alkaryl radicals, each $R^1$ is independently selected from hydrogen, $C_1$ up to about $C_{10}$ alkyl, cycloalkyl, aryl, aralkyl and alkaryl radicals, and $z = 3$ through II, inclusive, and 2 pyrrolidone. The amount of diluent employed should be confined to a molar ratio of about 1:1 up to about 25:1 with respect to the succinic acid or succinic anhydride component of the reaction mixture, in order to achieve desirable yields of 2-pyrrolidone product. Preferably, a molar ratio of diluent:succinic moiety of about 9:1 up to about 18:1 will be employed, with molar ratios betwen about 12:1 up to about 16:1 most preferred because optimum yields are obtained when ratios are maintained in that range.

Of the above listed diluents, water is preferred for its ready availability and demonstrated utility in producing 2-pyrrolidone in high yield.

CATALYST

The process of the invention is carried out employing a catalyst consisting of elemental palladium on an alumina support. Such catalytic materials are well known in the art. Generally, the alumina support will contain from about 0.1 up to about 15 percent by weight of elemental palladium, based on the total weight of support plus palladium. Preferably, elemental palladium will comprise about 1 up to about 10% by weight of the total catalyst (support plus palladium), with about 3 up to about 7% by weight of palladium most preferred for high product yields in convenient reaction times.

The total weight of elemental palladium on an alumina support which is employed for the reductive amination reaction of the invention can vary widely, as can readily be determined by those of skill in the art. When expressed as weight ratio of succinic moiety, i.e. succinic acid or succinic anhydride, to elemental palladium, a broad range of about 1:1 up to about 1000:1 is generally suitable. Preferably the weight ratio of succinic moiety to elemental palladium ranges from about 60:1 up to about 750:1, with a weight ratio of about 300:1 up to about 400:1 most preferred, for high product yield with efficient utilization of reagents.

REACTION PARAMETERS

The temperature at which the process of the invention can be carried out can be readily determined by those of skill in the art. In order to provide additional guidance, it is suggested that a temperature of about 200 up to about 300° C. be employed. The preferred reaction temperature is about 220 up to about 280° C., with temperatures ranging from about 240° to 265° C. most preferred because reaction proceeds at a reasonable rate and the production of undesirable by-products is held to a minimum.

Reaction time can vary over a wide range, but generally, for convenience, when reaction is carried out in the batch mode, reaction times of about 30 minutes up to about 18 hours are employed. For convenience, reaction times of about 30 minutes to about 8 horus are preferred, with reaction times of about 1 up to about 4 hours most preferred.

The reductive amination reaction of the present invention can also be carried out in the continuous mode employing a fixed bed reactor, fluidized bed reactor, or the like.

EXAMPLE

Succinic anhydride, catalyst and water were mixed in a stainless steel autoclave under a nitrogen atmosphere. Ammonium hydroxide was added and cooling provided to minimize the temperature rise which resulted from the exothermic reaction. The reactor was purged and then pressured with hydrogen, and maintained at the desired pressure level with a pressure regulator. The reaction was allowed to proceed for the desired length of time after reaching desired reaction conditions of temperature and pressure, after which the reactor was cooled with circulating water from an ice bath before opening. Samples of the reaction mixture were analyzed by gas liquid chromatograph (GLC) using a six foot by ¼ inch Tenax-GC column (60–80 mesh porous polymer; supplied by Alltech Associates, Inc., Applied Science Labs, 2051 Waukegan Rd., Deerfield, Ill. 60045) which was programmed from 100°–260° C. at 10°/minute. A weighed sample of tetrahydrofuran served as an internal standard for these analyses. Catalysts used were commercially available samples obtained from Strem Chemicals, Inc. (7 Mulliken Way, Newburyport, Mass. 01950), Alfa Products Thiokol/Ventron Div. (152 Andover St., Danvers, Mass. 01923), or Engelhard Corporation (Menlo Park CN 40, Edison, New Jersey 08818).

Results of three reference runs using 3 grams of 5 st. % palladium on carbon are shown in Table I and a number of runs using 5 st. % palladium on alumina are shown in Table II.

TABLE II

Reductive Amination of Succinic Anhydride (SA) Using 5% Pd/Al$_2$O$_3$ Catalyst

| Run | Wt. of Pd/Al$_2$O$_3$ Catalyst (g) | SA (mole) | NH$_3$ (mole) | Mole Ratio | H$_2$O (moles) | Temp., °C. | Press., psig | Time, Hrs. | 2-pyrrolidone Yield, % |
|---|---|---|---|---|---|---|---|---|---|
| 4 | 3.0 | 0.4 | 0.44 | 1.10 | 5.1 | 270 | 2000 | 3 | 62.9 |
| 5 | 3.0 | 0.4 | 0.88 | 2.21 | 6.1 | 275 | 2500 | 3 | 74.6 |
| 6 | 3.0 | 0.4 | 1.32 | 3.31 | 5.7 | 275 | 2500 | 3.5 | 76.2 |
| 7 | 3.0 | 0.4 | 1.76 | 4.40 | 5.3 | 270 | 2500 | 3 | 76.8 |
| 8 | 9.0 | 0.8 | 1.94 | 2.43 | 5.9 | 250 | 2500 | 2 | 75.6 |
| 9 | 3.0 | 0.4 | 0.44 | 1.10 | 6.5 | 290 | 2000 | 2 | 53.5 |
| 10 | 3.0 | 0.4 | 0.88 | 2.21 | 6.1 | 270 | 3000 | 2 | 75.5 |
| 11 | 3.0 | 0.6 | 1.59 | 2.65 | 5.7 | 270 | 3000 | 2.5 | 67.2 |
| 12 | 6.0 | 0.4 | 1.06 | 2.65 | 5.7 | 250 | 3000 | 2 | 62.9 |
| 13 | 6.0 | 0.4 | 1.06 | 2.65 | 5.7 | 250 | 3000 | 1.5 | 66.4 |
| 14 | 6.0 | 0.4 | 1.06 | 2.65 | 5.7 | 250 | 3000 | 2.5 | 62.9 |
| 15 | 3.0 (+0.5 g BPO$_4$) | 0.4 | 1.06 | 2.65 | 5.7 | 270 | 2500 | 3 | 77.8 |

TABLE I

Reductive amination of Succinic Anhydride (SA) Using 5% Pd/C catalyst

| Run | SA (mole) | NH$_3$ (mole) | NH$_3$/SA Ratio | H$_2$O (moles) | Temp., °C. | Press., psig | Time Hrs. | 2-pyrrolidone Yield, % |
|---|---|---|---|---|---|---|---|---|
| 1 | 0.4 | 0.45 | 1.12 | 5.2 | 250 | 2000 | 3 | 47.3 |
| 2 | 0.4 | 0.44 | 1.10 | 6.5 | 270 | 2000 | 2 | 48.3 |
| 3 | 0.4 | 0.44 | 1.10 | 5.1 | 270 | 2000 | 2.5 | 40.5 |

Yields in the range of 40 to 50% were obtained with the palladium on carbon catalyst under reaction conditions shown, while under comparable conditions using palladium on alumina a yield of about 63% was obtained (Run 4). Still further improvements in 2-pyrrolidone yield can be obtained by using a mole ratio of ammonia to succinic anhydride of at least 2:1, thus producing yields of 2-pyrrolidone in the range of 75% (Runs 4–7).

Comparison of runs 11 and 14 indicates that increased temperature gives improved yield of 2-pyrrolidone; however, run 9 demonstrates that temperatures of less than 290° C. are preferred. Comparison of runs 5 and 10 suggests that shorter reaction times can be employed when reaction is carried out at increased pressure with comparable yields of 20 pyrrolidone. In addition, comparison of run 15 with runs 5 and 6 indicates that the presence of boron phosphate has an additional beneficial effect on product yield.

That which is claimed is:

1. A process for the preparation of 2-pyrrolidone in which succinic acid or succinic anhydride is contacted with ammonia and hydrogen in the presence of at least one diluent, wherein the improvements comprise the use of a palladium on alumina catalyst and the use of a molar ratio of said ammonia to said succinic acid or succinic anhydride in the range of about 1:1 to 10:1.

2. A process in accordance with claim 1 wherein said diluent is selected from the group consisting of:
    water;
    ethers having the formulae:

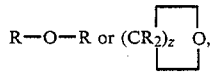

wherein each R is independently selected from the group consisting of alkyl, cycloalkyl, aryl, aralkyl and alkaryl radicals, having 1 to 10 carbon atoms, each R' is independently selected from the group consisting of H, alkyl, cycloalkyl, aryl, aralkyl and alkaryl radicals having 1 to 10 carbon atoms, and z = 3 through 11, inclusive; and 2-pyrrolidone.

3. A process in accordance with claim 2 wherein said diluent is water.

4. A process in accordance with claim 3 wherein the molar ratio of water to succinic acid or succinic anhydride is about 1:1 to about 25:1.

5. A process in accordance with claim 1 wherein the weight ratio of succinic acid or succinic anhydride to elemental palladium of said catalyst is about 1:1 to about 1000:1.

6. A process in accordance with claim 1 wherein the molar ratio of ammonia to succinic acid or succinic anhydride is about 1.5:1 to about 5:1.

7. A process in accordance with claim 1 wherein said contacting takes place at a temperature of about 200° to about 300° C. and a pressure of at least 1000 psig for a reaction time of about 30 minutes to about 18 hours.

8. A process in accordance with claim 1 which is further carried out in the presence of boron phosphate.

9. A process in accordance with claim 1 wherein said diluent is water; wherein the molar ratio of said water to said succinic acid or succinic anhydride is about 12:1 to about 16:1, the molar ratio of said ammonia to said succinic acid or succinic anhydride is about 1.5:1 to about 5:1, the weight ratio of said elemental palladium to said succinic acid or succinic anhydride is about 1:300 to about 1:400 and wherein the reaction temperature is about 220° C. to 280° C., reaction time is about 1 to 4 hours, and reaction pressure is about 1,500 to about 3,000 psig.

* * * * *